(12) United States Patent
Xu

(10) Patent No.: US 10,610,234 B2
(45) Date of Patent: Apr. 7, 2020

(54) OPEN-CLOSE-REPEATABLE ROTATABLE HEMOCLIP FOR THE GASTROINTESTINAL TRACT WITH ELECTROCOAGULATION

(71) Applicant: Zhejiang Chuangxiang Medical Technology Co., Ltd., Hangzhou (CN)

(72) Inventor: Qing Xu, Hangzhou (CN)

(73) Assignee: ZHEJIANG CHUANGXIANG MEDICAL TECHNOLOGY CO., LTD., Hangzhou (CN)

( * ) Notice: Subject to any disclaimer, the term of this patent is extended or adjusted under 35 U.S.C. 154(b) by 316 days.

(21) Appl. No.: 15/810,155

(22) Filed: Nov. 13, 2017

(65) Prior Publication Data

US 2018/0132855 A1     May 17, 2018

(30) Foreign Application Priority Data

Nov. 15, 2016 (CN) .......................... 2016 1 1004337
Nov. 15, 2016 (CN) .......................... 2016 1 1004338

(51) Int. Cl.
    *A61B 18/14*      (2006.01)
    *A61B 17/12*      (2006.01)
    (Continued)

(52) U.S. Cl.
    CPC .......... *A61B 17/122* (2013.01); *A61B 17/128* (2013.01); *A61B 17/1285* (2013.01);
    (Continued)

(58) Field of Classification Search
    CPC . A61B 17/122; A61B 17/128; A61B 17/1285; A61B 18/12; A61B 18/1442;
    (Continued)

(56) References Cited

U.S. PATENT DOCUMENTS 5,456,683 A * 10/1995 Fritzsch ............. A61B 18/1442
    606/41
5,716,354 A * 2/1998 Hluchy .............. A61B 18/1442
    606/46

(Continued)

FOREIGN PATENT DOCUMENTS

DE      10011292 A1    9/2000
EP        0584723 A1    3/1994

(Continued)

*Primary Examiner* — Michael F Peffley
(74) *Attorney, Agent, or Firm* — Bayramoglu Law Offices LLC

(57) ABSTRACT

An open-close-repeatable rotatable hemoclip for the gastrointestinal tract with electrocoagulation is provided by the present invention, including a clamping assembly, a tightening assembly, an insulating outer tube assembly and a handle assembly. The clamping assembly is rotatable and open-close-repeatable under actions of the handle assembly, the insulating outer tube assembly and the tightening assembly. An electrode is arranged inside the handle assembly. The electrode is electrically connected to the clamping assembly through the insulating outer tube assembly and the tightening assembly. The hemoclip of the present invention can be easily rotated inside the human body according to various angle requirements. When a flaky and irregular bleeding occurs, a high frequency electric power can be introduced for an electrocoagulation hemostasis.

7 Claims, 7 Drawing Sheets

(51) Int. Cl.
*A61B 17/122* (2006.01)
*A61B 17/128* (2006.01)
*A61B 18/12* (2006.01)
*A61B 18/00* (2006.01)
*A61B 17/00* (2006.01)

(52) U.S. Cl.
CPC .......... *A61B 18/12* (2013.01); *A61B 18/1442* (2013.01); *A61B 18/1482* (2013.01); *A61B 2017/00353* (2013.01); *A61B 2017/00438* (2013.01); *A61B 2017/00469* (2013.01); *A61B 2017/00477* (2013.01); *A61B 2017/00584* (2013.01); *A61B 2017/12004* (2013.01); *A61B 2018/00083* (2013.01); *A61B 2018/00404* (2013.01); *A61B 2018/00482* (2013.01); *A61B 2018/00589* (2013.01); *A61B 2018/00595* (2013.01); *A61B 2018/00952* (2013.01); *A61B 2018/1475* (2013.01)

(58) Field of Classification Search
CPC ...... A61B 18/1482; A61B 2017/00353; A61B 2017/00438; A61B 2017/00469; A61B 2017/00477; A61B 2017/00584; A61B 2017/12004; A61B 2018/00083; A61B 2018/00404; A61B 2018/00482; A61B 2018/00589; A61B 2018/00595; A61B 2018/00952; A61B 2018/1475
See application file for complete search history.

(56) References Cited

U.S. PATENT DOCUMENTS

| | | | |
|---|---|---|---|
| 6,767,348 B2 * | 7/2004 | Nakada | A61B 18/1442 606/46 |
| 7,824,407 B2 * | 11/2010 | Yamamoto | A61B 18/1445 606/46 |
| 2005/0075631 A1 * | 4/2005 | Kidooka | A61B 10/06 606/51 |

FOREIGN PATENT DOCUMENTS

| | | |
|---|---|---|
| WO | 9614020 A1 | 5/1996 |
| WO | 0197696 A1 | 12/2001 |
| WO | 2008073567 A1 | 6/2008 |

* cited by examiner

OPEN-CLOSE-REPEATABLE ROTATABLE HEMOCLIP FOR THE GASTROINTESTINAL TRACT WITH ELECTROCOAGULATION

CROSS REFERENCE TO RELATED APPLICATIONS

This application is based upon and claims priority to Chinese Patent Application No. 201611004338.X filed on Nov. 15, 2016, and Chinese Patent Application No. 201611004337.5 filed on Nov. 15, 2016, the entire contents of which are incorporated herein by reference.

TECHNICAL FIELD

The present invention relates to the field of medical instrument technology, and more particularly to an open-close-repeatable rotatable hemoclip for the gastrointestinal tract with electrocoagulation.

BACKGROUND

Conventional endoscopic hemostasis clips have become one of the most widely used hemostasis methods for critically ill patients due to the advantages of small trauma, fast hemostasis speed, low incidence of rebleeding, less complications and exact effect etc. The hemostatic mechanism of the existing metal hemoclip is the same as that of the surgical blood vessel ligation or suture, and is a physical and mechanical method. Under the mechanical force generated when the hemoclip is closed, the surrounding tissues and the bleeding blood vessel are ligated at the same time, so as to close the bleeding blood vessel to block the blood flow and realize the purpose of hemostasis. This method is suitable for the hemostasis treatment of non-variceal active bleeding and visible residual lesions of blood vessel, and has been recognized by the doctors and patients. The hemoclip can also close the mucosa of the gastrointestinal tract to promote wound healing. However, the hemoclip is not effective for the irregular bleeding and fine bleeding points on the surface of gastrointestinal tract, and the cost thereof is high for a large-scale use, which increases the patient's medical expenses. Generally, an electrocoagulation hemostasis is applied to the irregular bleeding points on the surface through high frequency electric power introduced by the endoscopic high-frequency surgical instruments, and a function of marking before the operation of gastrointestinal mucosa dissection is fulfilled. However, since the high-frequency surgical instruments do not have the function of clamping and closing, the massive hemorrhage of blood vessel cannot be closed, so that a reoperation is required. Therefore, the operation time is extended and patients suffer more.

SUMMARY OF THE INVENTION

The present invention aims to provide an open-close-repeatable rotatable hemoclip for the gastrointestinal tract with electrocoagulation to solve the drawbacks of the prior art.

The technical solutions of the present invention are as follows.

An open-close-repeatable rotatable hemoclip for the gastrointestinal tract with electrocoagulation includes a clamping assembly, a tightening assembly, an insulating outer tube assembly and a handle assembly.

The clamping assembly is rotatable, open-close-repeatable and releasable under actions of the handle assembly, the insulating outer tube assembly and the tightening assembly. An electrode is arranged inside the handle assembly. The electrode is electrically connected to the clamping assembly through the insulating outer tube assembly and the tightening assembly.

Furthermore, the clamping assembly includes two oppositely arranged metal clips.

The tightening assembly includes a tightening tube, a connecting rod, a releasing piece and a fixing base. A fixing pin is arranged inside a front portion of the tightening tube. Two symmetrical openings are arranged on a wall of a middle-lower portion of the tightening tube. A wall of a portion in front of the two symmetrical openings is respectively pre-provided with a slot matched with a tail end of the metal clips. In the tightening tube, the rear portions of the two metal clips are connected to the connecting rod through a movable pin. A front portion of the releasing piece and a tail portion of the tightening tube are relatively fixed in an axial direction, and relatively rotatably connected in a radial direction. A rear portion of the releasing piece and the fixing base are relatively fixed in the axial direction, and relatively rotatably connected in the radial direction. The connecting rod passes through the tightening tube and the releasing piece, successively.

The insulating outer tube assembly includes an electric cutting wire, a guide tube and a spring hose. A tail portion of the electric cutting wire is arranged inside the guide tube. An outer wall of the tail portion of the electric cutting wire closely contacts an inner wall of the guide tube. The electric cutting wire is arranged inside the spring hose. A front end of the electric cutting wire is connected to a rear end of the connecting rod. A front end of the spring hose is connected to a rear end of the fixing base.

The handle assembly includes a thumb ring, a handle, a slide ring, a rotary wheel, an electrode and an electrode holder. The thumb ring is arranged at a rear end of the handle. The slide ring is arranged on the handle. The rotary wheel is arranged at a front portion of the handle. The electrode holder is arranged inside the slide ring. The electrode is arranged inside the electrode holder. A rear end of the spring hose is connected to a front end of the handle. The guide tube deeply extends into the handle and the electrode holder. The guide tube and the rotary wheel are relatively fixed in the radial direction and relatively slidably connected in the axial direction. Also, the guide tube is tightly pressed by the electrode. The guide tube is driven to rotate with respect to the handle by rotating the rotary wheel so as to realize a rotation of the metal clips. The slide ring slides back and forth on the handle to drive the guide tube to move back and forth, so as to drive the clamping assembly to reciprocate in the tightening tube. The metal clips are opened or closed, accordingly. When a predetermined tensile force is exerted, the connecting rod and the movable pin are separated, so as to drive a separation of the releasing piece and the tightening tube. The tail end of each metal clip is fixed in a pre-set slot of the tightening tube. The metal clips are closed and self-locked to realize a release of the metal clips.

The tightening tube, the fixing base, the spring hose, the releasing piece, the metal clips, the movable pin, the connecting rod, the electric cutting wire and the guide tube are made of a metal material. An inner wall and an outer wall of the tightening tube, an inner wall and an outer wall of the fixing base, and an outer wall of the spring hose are all provided with an insulating coating.

Furthermore, the electrode holder and the electrode are provided with matching threads, and the threads on the electrode are screwed into the electrode holder.

Furthermore, a pressure contact is applied between the electric cutting wire and the guide tube to make the outer wall of the tail portion of the electric cutting wire closely contact the inner wall of the guide tube. The threads on the electrode are screwed into the electrode holder to tightly press the outer wall of the guide tube.

Furthermore, both tail ends of the two oppositely arranged metal clips are provided with a bent part. A head end of each metal clip has a quarter-spherical shape and is provided with a tooth-shaped part, and tooth-shaped parts of the metal clips are engaged with each other. A front portion of each metal clip is gradually widened from front to back. A curved part is arranged between the front portion and a rear portion of each metal clip. The rear portion of each metal clip is a large arc. Also, the rear portion of each metal clip is provided with a hole. Each metal clip is connected to the movable pin through the hole.

Furthermore, a front end of the connecting rod is provided with a locking slot, and both sides of the locking slot are provided with a pin hole. The locking slot is connected to the movable pin through the pin hole. The two metal clips are fixed in the locking slot. A lower portion of a front end of the connecting rod is provided with a step. A rear end of the connecting rod is provided with a counter bore. A front end of the electric cutting wire is connected within the counter bore. When a predetermined tensile force is exerted, the pin hole of the connecting rod is broken and the connecting rod is separated from the movable pin. While the connecting rod is being retracted, a disengagement of the releasing piece and the tightening tube is driven by the step.

Furthermore, the overall releasing piece has a cylindrical shape. A head end of the releasing piece consists of two projecting steps. The two projecting steps are hung on an opening of the tightening tube. An axial outer diameter of a front portion of the releasing piece is matched with an inner diameter of the tail portion of the tightening tube to realize a relative fixation in the axial direction and a relative rotary connection in the radial direction. A rear portion of the releasing piece is provided with a step shaft, and the step shaft is matched with a step hole in the fixing base to realize the relative fixation in the axial direction and the relative rotary connection in the radial direction. When a predetermined tensile force is exerted, the head end of the releasing piece is driven by the connecting rod to separate from the tightening tube.

Furthermore, the inner wall and the outer wall of the tightening tube and the fixing base are covered with the insulating coating through a brushing process or a baking process. The outer wall of the spring hose is plastic-coated with a layer of insulating coating through the plastic coating process.

Furthermore, the insulating coating includes polytetrafluoroethylene, fluorinated ethylene-propylene, ethylene-tetrafluoroethylene copolymer, polyvinylidene fluoride or silicone rubber.

The advantages of the present invention are as follows.

The hemoclip of the present invention can be easily rotated inside the human body according to various angles so as to conform to the doctor's operating habits. When flaky and irregular bleeding occurs, a high frequency electrical power can be introduced for an electrocoagulation hemostasis. When spraying bleeding occurs, with the function of clamping hemostasis of the hemoclip, after successful positioning, the metal clips are released by pulling the handle assembly and close the bleeding point and wound. When the operative region needs to be determined before the operation, the electrocoagulation function can be used to mark the lesion region and the incision region to prevent influences on other healthy tissues. The hemoclips of the present invention are easy to operate, which shortens operation time, and reduces the pain and the medical costs of the patients.

DETAILED DESCRIPTION OF THE INVENTION

Figure 1:
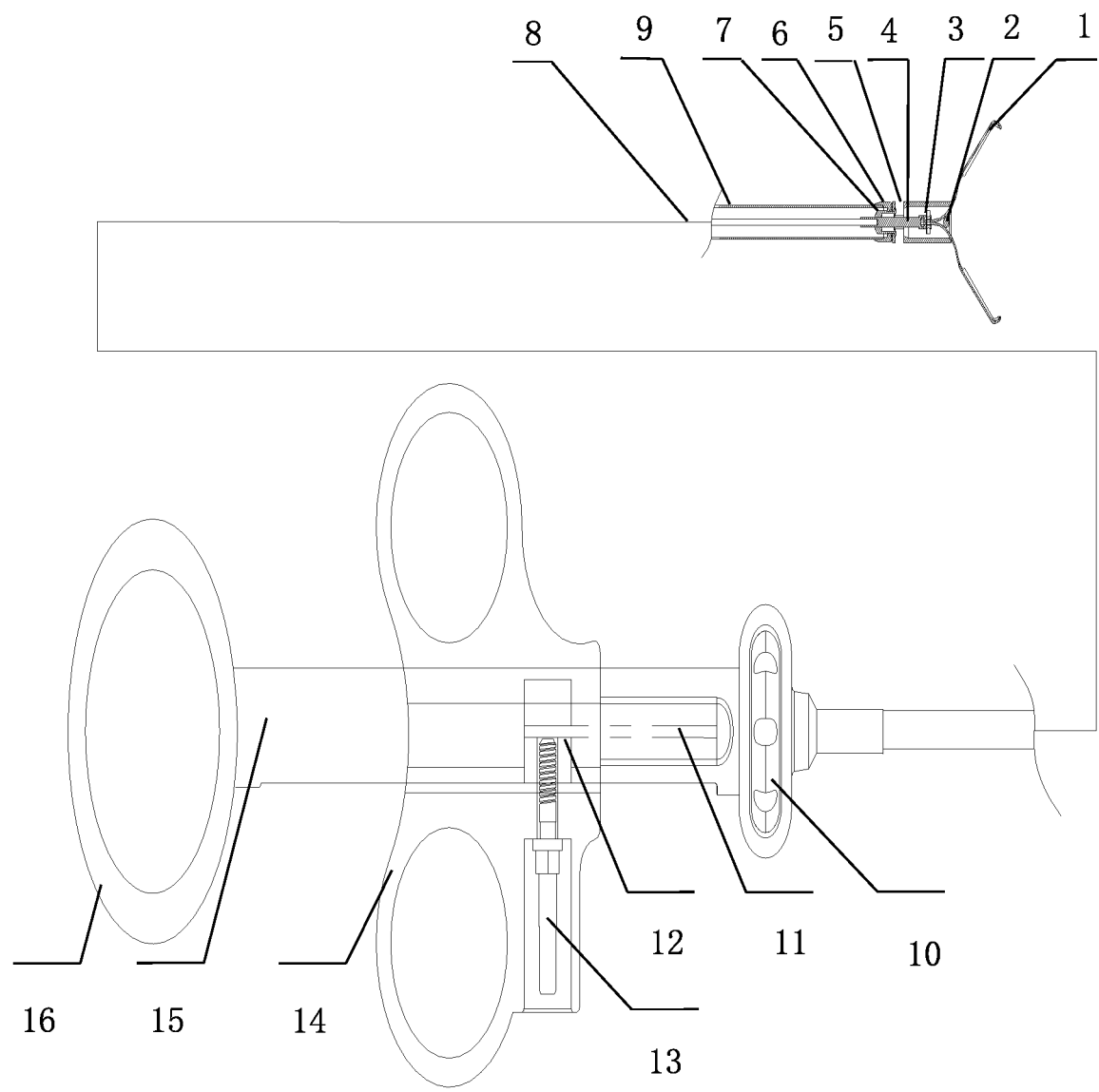
FIG. 1 is a structural schematic diagram of the hemoclip of the present invention.
Figure 2:
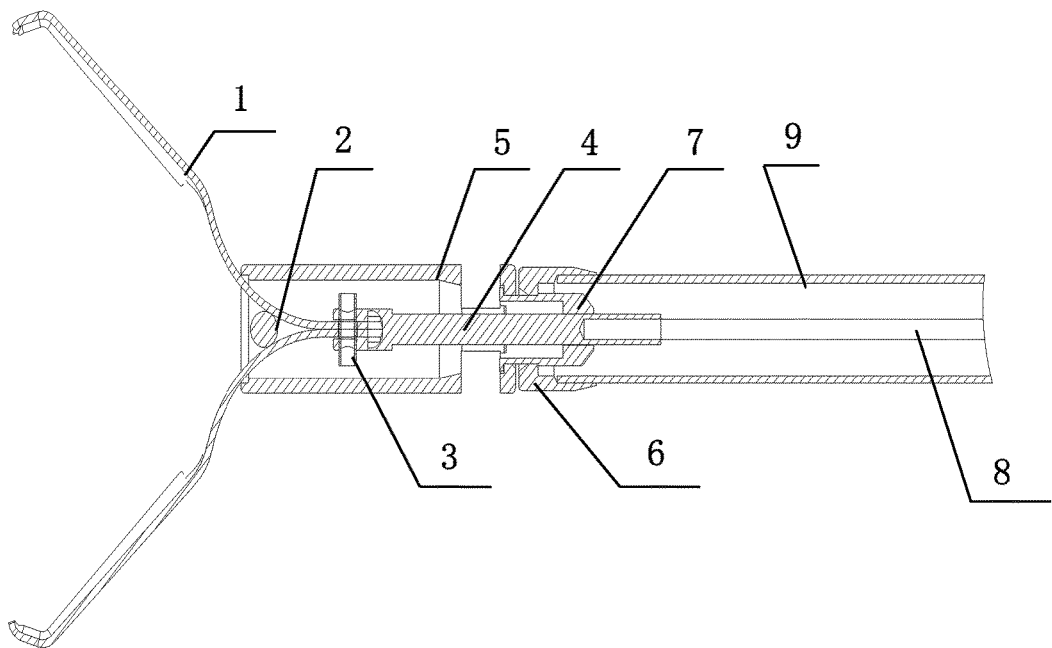
FIG. 2 is a schematic diagram showing an opening state of the metal clip.
Figure 3:
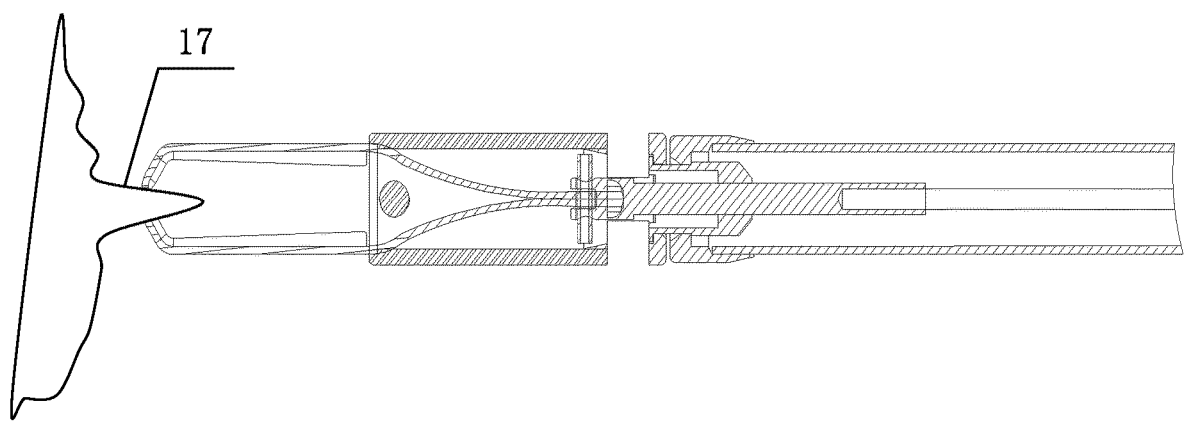
FIG. 3 is a schematic diagram showing a closing state of the metal clip.
Figure 4:
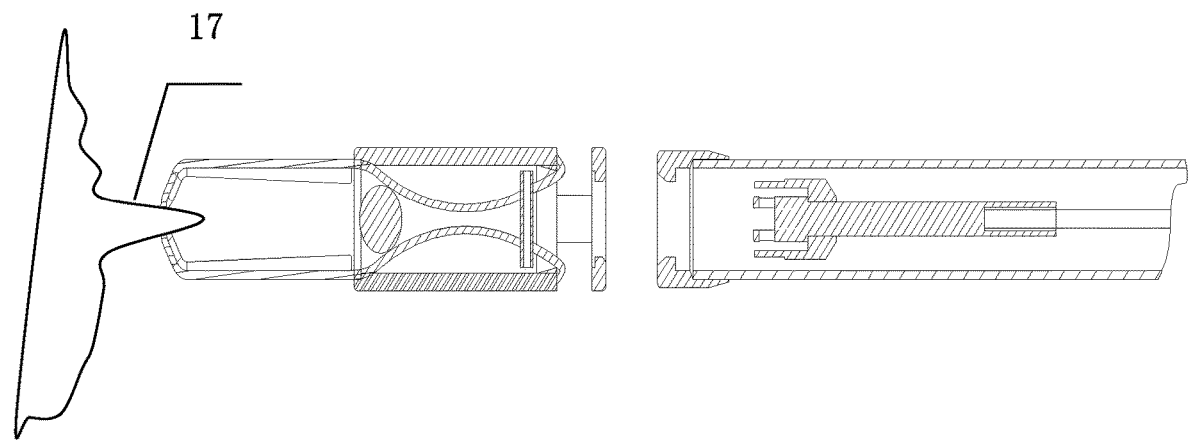
FIG. 4 is a schematic diagram showing releasing and self-locking of the metal clip.

The present invention will be further described with reference to the embodiments and the drawings hereinafter. The following embodiments are merely intended to illustrate the present invention, rather than limit the implementation scope of the present invention.

An open-close-repeatable rotatable hemoclip for the gastrointestinal tract with electrocoagulation, as shown in FIGS. 1-4, includes a clamping assembly, a tightening assembly, an insulating outer tube assembly and a handle assembly.

The clamping assembly includes two oppositely arranged metal clips 1.

The tightening assembly includes a tightening tube 5, a connecting rod 4, a releasing piece 7 and a fixing base 6. A fixing pin 2 is arranged inside a front portion of the tightening tube 5. Two symmetrical openings are arranged on a wall of a middle-lower portion of the tightening tube 5. A wall of a portion in front of the two symmetrical openings is respectively pre-provided with a slot matched with a tail end of each metal clip 1. In the tightening tube 5, the rear portions of the two metal clips 1 are connected to the connecting rod 4 through a movable pin 3. A front portion of the releasing piece 7 and a rear portion of the tightening tube 5 are relatively fixed in an axial direction, and relatively rotatably connected in a radial direction. A rear portion of the releasing piece 7 and the fixing base 6 are relatively fixed in the axial direction, and relatively rotatably connected in the radial direction. The connecting rod 4 passes through the tightening tube 5 and the releasing piece 7, successively.

The insulating outer tube assembly includes an electric cutting wire 8, a guide tube 11 and a spring hose 9. A tail portion of the electric cutting wire 8 is arranged inside the guide tube 11. An outer wall of the tail portion of the electric cutting wire 8 closely contacts an inner wall of the guide tube 11. The electric cutting wire 8 is arranged inside the spring hose 9. A front end of the electric cutting wire 8 is connected to a rear end of the connecting rod 4. A front end of the spring hose 9 is connected to a rear end of the fixing base 6.

The handle assembly includes a thumb ring 16, a handle 15, a slide ring 14, a rotary wheel 10, an electrode 13 and an electrode holder 12. The thumb ring 16 is arranged at a rear end of the handle 15. The slide ring 14 is arranged on the handle 15. The rotary wheel 10 is arranged at a front portion of the handle 15. The electrode holder 12 is arranged inside the slide ring 14. The electrode 13 is arranged inside the electrode holder 12. The electrode holder 12 and the electrode 13 are provided with matching threads, and the threads on the electrode 13 are screwed into the electrode holder 12. A rear end of the spring hose 9 is connected to a front end of the handle 15. The guide tube 11 deeply extends into the handle 15 and the electrode holder 12. The guide tube 11 and the rotary wheel 10 are relatively fixed in the radial direction and relatively slidably connected in the axial direction. Also, the guide tube 11 is tightly pressed by the electrode 13.

The guide tube 11 is driven to rotate with respect to the handle 15 by rotating the rotary wheel 10 so as to realize a rotation of the metal clips 1. The slide ring 14 slides back and forth on the handle 15 to drive the guide tube 11 to move back and forth, so as to drive the clamping assembly to reciprocate in the tightening tube 11. The metal clips 1 are opened or closed, accordingly. When a predetermined tensile force is exerted, the connecting rod 4 and the movable pin 3 are separated, so as to drive a separation of the releasing piece 7 and the tightening tube 5. The tail end of each metal clip 1 is fixed in a preset slot of the tightening tube 5. The metal clips 1 are closed and self-locked to realize a release of the metal clips 1.

The tightening tube 5, the fixing base 6, the spring hose 9, the releasing piece 7, the metal clips 1, the movable pin 3, the connecting rod 4, the electric cutting wire 8 and the guide tube 11 are all made of a metal material. An inner wall and an outer wall of the tightening tube 5, an inner wall and an outer wall of the fixing base 6, and an outer wall of the spring hose 9 are all provided with an insulating coating. The inner wall and the outer wall of the tightening tube 5 and the fixing base 6 are covered with the insulating coating through a brushing process or a baking process etc. The outer wall of the spring hose 9 is plastic-coated with a layer of insulating coating through the plastic coating process. The insulating coating includes insulating polymer materials such as polytetrafluoroethylene, fluorinated ethylene-propylene, ethylene-tetrafluoroethylene copolymer, polyvinylidene fluoride or silicone rubber etc. When the electric power is introduced, the insulating coating can prevent the lower half portion, except for the metal clip 1, from burning tissues by mistake, thereby avoiding or reducing touching other healthy tissues during the electrocoagulation.

Figure 5:
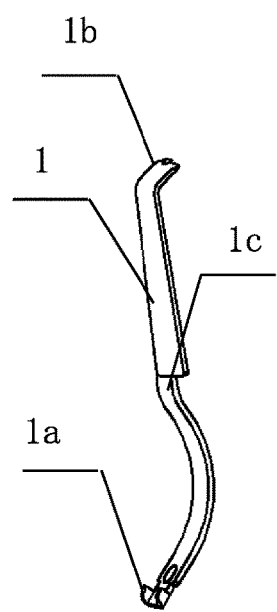
FIG. 5 is a structural schematic diagram of the metal clip.

As shown in FIG. 5, the tail end of each metal clip 1 is provided with a bent part 1a to avoid a wobble of the clamping assembly. A head end 1b of each metal clip 1 has a quarter-spherical shape and is provided with a tooth-shaped part, and tooth-shaped parts of metal clips 1 are engaged with each other. A front portion of the metal clip 1 is gradually widened from front to back. A curved part 1c is arranged between the front portion and a rear portion of the metal clip 1 to increase the strength of the metal clip 1. The rear portion of the metal clip 1 is a large arc, and the strength and elasticity are increased due to the arc structure. Also, the rear portion of the metal clip 1 is provided with a hole. The metal clip 1 is connected to the movable pin 3 through the hole. When the product is closed and passes through the endoscope, the head portion has a hemisphere shape, so as to pass through the channel of the endoscope easily and avoid damage to the product.

Figure 6:
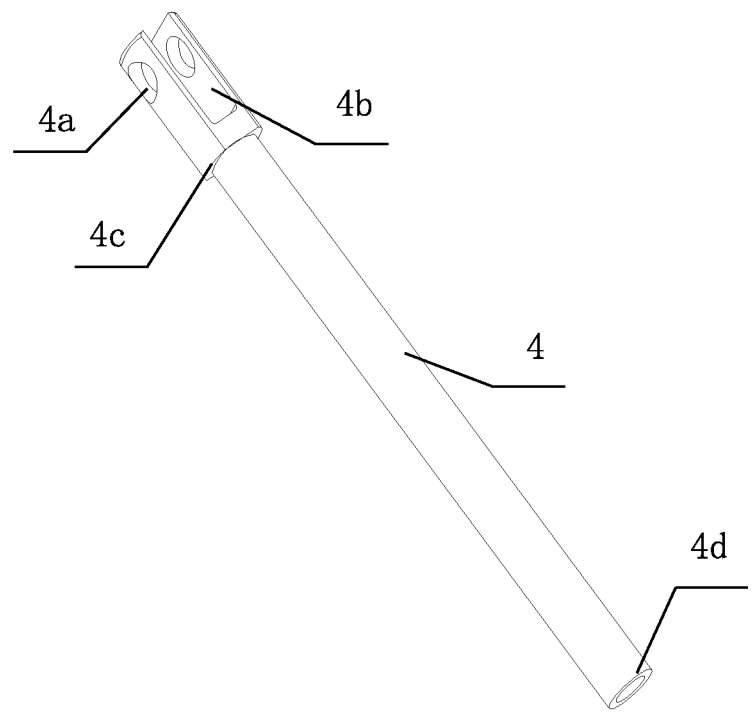
FIG. 6 is a structural schematic diagram of the connecting rod.

As shown in FIG. 6, a front end of the connecting rod 4 is provided with a locking slot 4b, and both sides of the locking slot 4b are provided with a pin hole 4a. The locking slot 4b is connected to the movable pin 3 through the pin holes 4a. The two metal clips 1 are fixed in the locking slot 4b to ensure a relative fixation when the metal clips 1 are opened repeatedly. A lower portion of a front end of the connecting rod 4 is provided with a step 4c. A rear end of the connecting rod 4 is provided with a counter bore 4d. A front end of the electric cutting wire 8 is connected within the counter bore 4d through welding. When a predetermined tensile force is exerted, the pin hole 4a of the connecting rod 4 is broken and the connecting rod 4 is separated from the movable pin 3. While the connecting rod 4 is being retracted, a disengagement of the releasing piece 7 and the tightening tube 5 is driven by the step 4c, so as to release the metal clips 1 and realize the intention of hemostasis.

Figure 7:
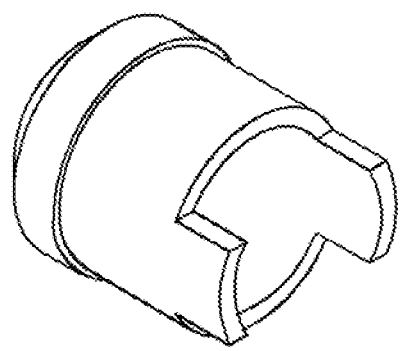
FIG. 7 is a structural schematic diagram of the releasing piece.

As shown in FIG. 7, the overall releasing piece 7 has a cylindrical shape, which can reduce the friction force during the rotation. A head end 7a of the releasing piece 7 consists of two projecting steps. The two projecting steps are hung on an opening of the tightening tube 5. An axial outer diameter of a front portion of the releasing piece 7 is matched with an inner diameter of the tail portion of the tightening tube 5 to realize a relative fixation in the axial direction and a relative rotary connection in the radial direction. A rear portion 7b of the releasing piece 7 is provided with a step shaft, and the step shaft is matched with a step hole in the fixing base 6 to realize the relative fixation in the axial direction and the relative rotary connection in the radial direction to avoid a disengagement toward the head of the metal clip. When a predetermined tensile force is exerted, the head end 7a of the releasing piece 7 is driven by the connecting rod 4 to separate from the tightening tube 5.

Figure 8:
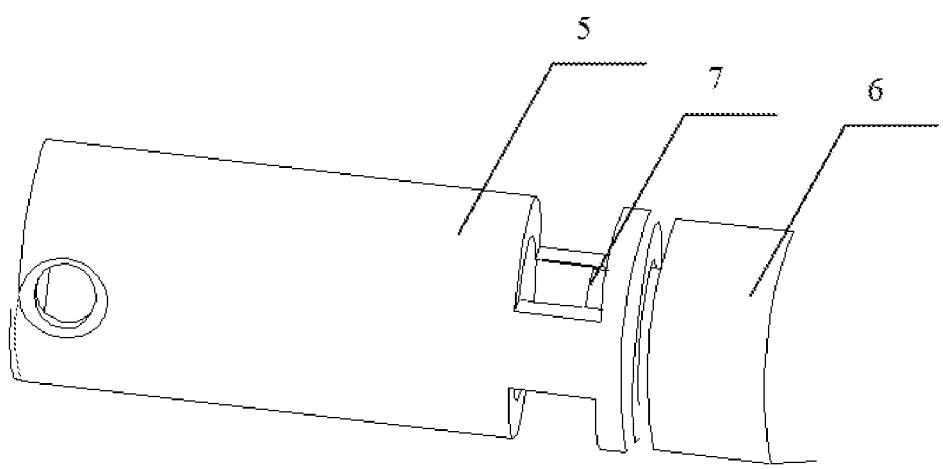
FIG. 8 is a structural schematic diagram of the tightening assembly.

As shown in FIG. 8, the front portion of the releasing piece 7 and the tail portion of the tightening tube 5 are relatively fixed in the axial direction and relatively rotatably connected in the radial direction. The rear portion 7b of the releasing piece 7 and the fixing base 6 are relatively fixed in the axial direction and relatively rotatably connected in the radial direction. The releasing piece 7 overlaps with the tail portion of the tightening tube 5 and the fixing base 6, to form a combination of which internal parts and external parts cooperate with each other, so as to achieve the function of rotation. The overall retention length is reduced to about 12.5 mm, so that the retention length inside the human body is shortened.

Figure 9:
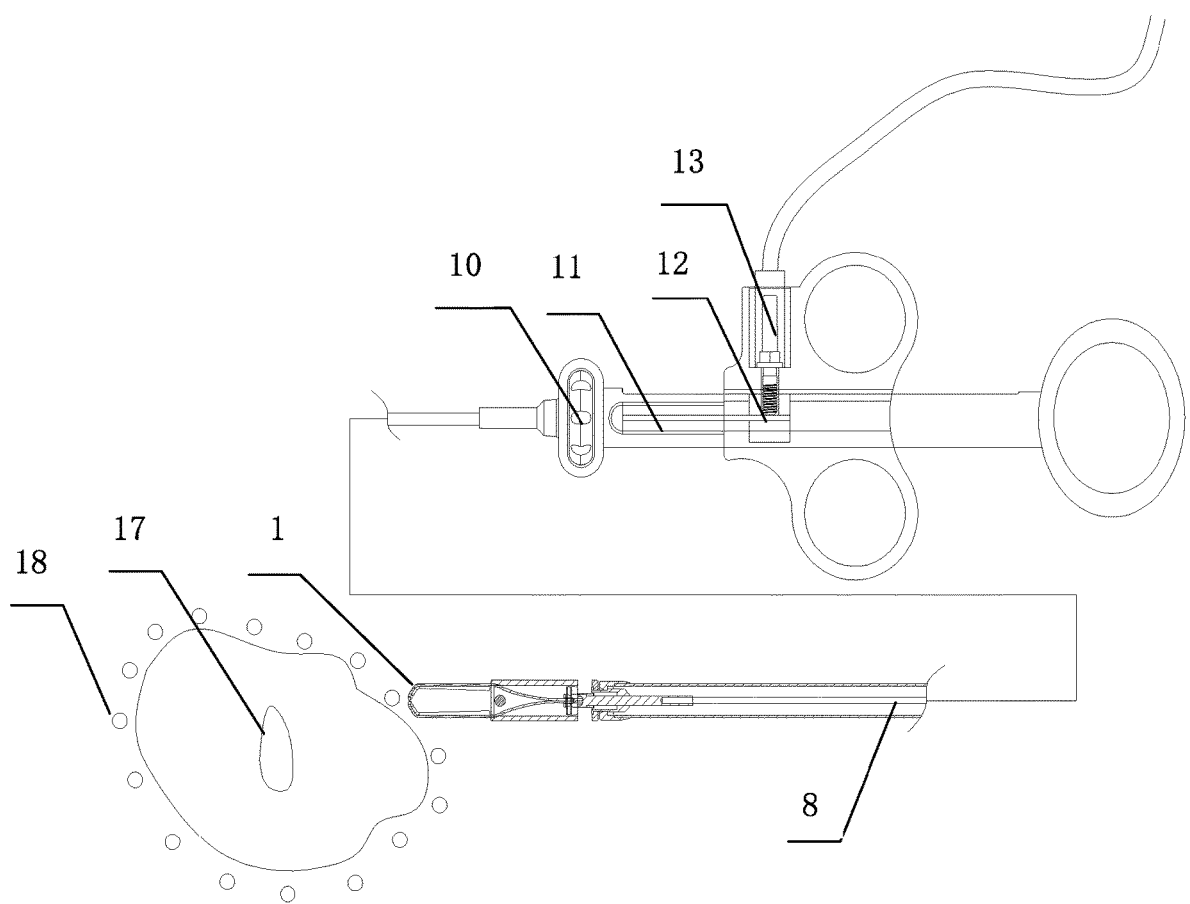
FIG. 9 is a schematic diagram showing the electrocoagulation when electric power is supplied and the marking of the hemoclip of the present invention.
Figure 10:
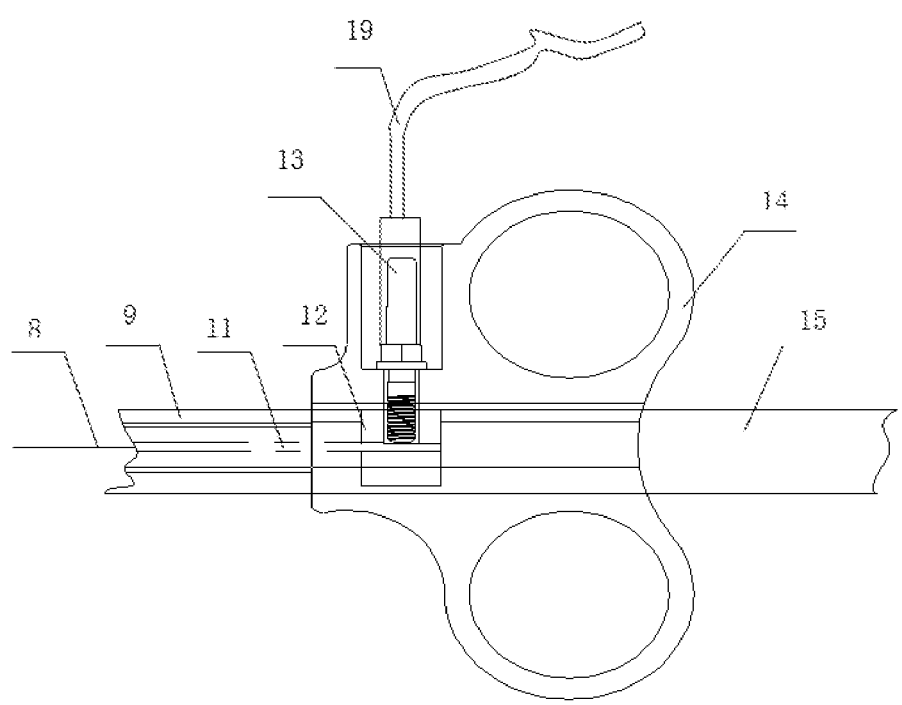
FIG. 10 is a schematic diagram showing the structure of the handle assembly when electric power is supplied.

As shown in FIGS. 9 and 10, when the marking and the electrocoagulation are required, one end of the high-frequency cable 19 is inserted into the electrode 13, and the other end of the high-frequency cable is connected to a high-frequency electrotome. The lesion region is determined by the marks 18 according to the actual demand of the operation to help the doctor to determine the size of the lesion and the surgical method. During the implementation process, if an exudation of blood occurs, the voltage is adjusted according to the actual situation to realize a coagulation of blood on the exudation points. After the electrocoagulation is completed, if a large blood vessel is found to be bleeding, the bleeding point 17 can be closed by means of the closing function of metal clips 1. The function of repeatable opening and closing of the metal clips 1 is realized by pushing and pulling the slide ring 14. The bleeding point 17 is pre-clamped, and after the bleeding point 17 is confirmed, the metal clip 1 is released, so that the bleeding point 17 and wound are closed. By doing so, the operation time is shortened, the patients can suffer less and medical costs are reduced.

I claim:
1. An open-close-repeatable rotatable hemoclip for the gastrointestinal tract with electrocoagulation, comprising:
   a clamping assembly;
   a tightening assembly;
   an insulating outer tube assembly, and
   a handle assembly;
   wherein, the clamping assembly is rotatable, open-close-repeatable and releasable under actions of the handle assembly, the insulating outer tube assembly and the tightening assembly;
   an electrode is arranged inside the handle assembly;
   the electrode is electrically connected to the clamping assembly through the insulating outer tube assembly and the tightening assembly, wherein
   the clamping assembly includes two oppositely arranged metal clips;
   the tightening assembly includes a tightening tube, a connecting rod, a releasing piece and a fixing base;
   wherein, a fixing pin is arranged inside a front portion of the tightening tube;
   two symmetrical openings are arranged on a wall of a middle-lower portion of the tightening tube;
   a wall of a portion in front of the two symmetrical openings is respectively pre-provided with a slot matched with a tail end of each metal clip;
   in the tightening tube, rear portions of the two metal clips are connected to the connecting rod through a movable pin;
   a front portion of the releasing piece and a tail portion of the tightening tube are relatively fixed in an axial direction, and relatively rotatably connected in a radial direction;
   a rear portion of the releasing piece and the fixing base are relatively fixed in the axial direction, and relatively rotatably connected in the radial direction;
   the connecting rod passes through the tightening tube and the releasing piece, successively;
   the insulating outer tube assembly includes an electric cutting wire, a guide tube and a spring hose;
   wherein, a tail portion of the electric cutting wire is arranged inside the guide tube;
   an outer wall of the tail portion of the electric cutting wire closely contacts an inner wall of the guide tube;
   the electric cutting wire is arranged inside the spring hose;
   a front end of the electric cutting wire is connected to a rear end of the connecting rod;
   a front end of the spring hose is connected to a rear end of the fixing base;
   the handle assembly includes a thumb ring, a handle, a slide ring, a rotary wheel, an electrode and an electrode holder;
   wherein, the thumb ring is arranged at a rear end of the handle;
   the slide ring is arranged on the handle;
   the rotary wheel is arranged at a front portion of the handle;
   the electrode holder is arranged inside the slide ring;
   the electrode is arranged inside the electrode holder;
   a rear end of the spring hose is connected to a front end of the handle;
   the guide tube deeply extends into the handle and the electrode holder;
   the guide tube and the rotary wheel are relatively fixed in the radial direction and relatively slidably connected in the axial direction;
   the guide tube is tightly pressed by the electrode;
   the guide tube is driven to rotate with respect to the handle by rotating the rotary wheel so as to realize a rotation of the metal clips;
   the slide ring slides back and forth on the handle to drive the guide tube to move back and forth, so as to drive the clamping assembly to reciprocate in the tightening tube;
   the metal clips are opened or closed when the clamping assembly reciprocates;
   when a predetermined tensile force is exerted, the connecting rod and the movable pin are separated, so as to drive a separation of the releasing piece and the tightening tube;
   the tail end of each metal clip is fixed in a pre-set slot of the tightening tube;
   the metal clips are closed and self-locked to realize a release of the metal clips;
   the tightening tube, the fixing base, the spring hose, the releasing piece, the metal clips, the movable pin, the connecting rod, the electric cutting wire and the guide tube are made of a metal material; and
   an inner wall and an outer wall of the tightening tube, an inner wall and an outer wall of the fixing base, and an outer wall of the spring hose are all provided with an insulating coating.

2. The open-close-repeatable rotatable hemoclip for the gastrointestinal tract with electrocoagulation of claim 1, wherein
   the electrode holder and the electrode are provided with matching threads, and the threads on the electrode are screwed into the electrode holder.

3. The open-close-repeatable rotatable hemoclip for the gastrointestinal tract with electrocoagulation of claim 1, wherein
   both tail ends of the two oppositely arranged metal clips are provided with a bent part;
   a head end of each metal clip has a quarter-spherical shape;
   the head end of each metal clip is provided with a tooth-shaped part, and tooth-shaped parts of the metal clips are engaged with each other;
   a front portion of each metal clip is gradually widened from front to back;
   a curved part is arranged between the front portion and a rear portion of each metal clip;
   the rear portion of each metal clip is a large arc;
   the rear portion of each metal clip is provided with a hole; and
   each metal clip is connected to the movable pin through the hole.

4. The open-close-repeatable rotatable hemoclip for the gastrointestinal tract with electrocoagulation of claim 1, wherein
   a front end of the connecting rod is provided with a locking slot, and both sides of the locking slot are provided with a pin hole;
   the locking slot is connected to the movable pin through the pin hole;
   the two metal clips are fixed in the locking slot;
   a lower portion of a front end of the connecting rod is provided with a step;

a rear end of the connecting rod is provided with a counter bore;

a front end of the electric cutting wire is connected within the counter bore;

when a predetermined tensile force is exerted, the pin hole of the connecting rod is broken and the connecting rod is separated from the movable pin; and while the connecting rod is being retracted, a disengagement of the releasing piece and the tightening tube is driven by the step.

5. The open-close-repeatable rotatable hemoclip for the gastrointestinal tract with electrocoagulation of claim 1, wherein an overall releasing piece has a cylindrical shape;

a head end of the releasing piece consists of two projecting steps;

the two projecting steps are hung on an opening of the tightening tube;

an axial outer diameter of a front portion of the releasing piece is matched with an inner diameter of the tail portion of the tightening tube to realize a relative fixation in the axial direction and a relative rotary connection in the radial direction;

a rear portion of the releasing piece is provided with a step shaft;

the step shaft is matched with a step hole in the fixing base to realize the relative fixation in the axial direction and the relative rotary connection in the radial direction; and when a predetermined tensile force is exerted, the head end of the releasing piece is driven by the connecting rod to separate from the tightening tube.

6. The open-close-repeatable rotatable hemoclip for the gastrointestinal tract with electrocoagulation of claim 1, wherein the inner wall and the outer wall of the tightening tube and the inner wall and the outer wall of the fixing base are covered with the insulating coating through a brushing process or a baking process; and the outer wall of the spring hose is plastic-coated with a layer of insulating coating through the plastic coating process.

7. The open-close-repeatable rotatable hemoclip for the gastrointestinal tract with electrocoagulation of claim 6, wherein the insulating coating is selected from the group consisting of polytetrafluoroethylene, fluorinated ethylene-propylene, ethylene-tetrafluoroethylene copolymer, polyvinylidene fluoride and silicone rubber.

* * * * *